US010374350B2

United States Patent
Nakazono et al.

(10) Patent No.: US 10,374,350 B2
(45) Date of Patent: Aug. 6, 2019

(54) CONNECTOR, ELECTRIC WIRE WITH CONNECTOR, AND MEDICAL DEVICE SENSOR

(71) Applicant: TATSUTA Electric Wire & Cable Co., Ltd., Higashiosaka-shi (JP)

(72) Inventors: Syoji Nakazono, Kizugawa (JP); Kiyotaka Urashita, Kizugawa (JP)

(73) Assignee: TATSUTA Electric Wire & Cable Co., Ltd., Osaka (JP)

( * ) Notice: Subject to any disclaimer, the term of this patent is extended or adjusted under 35 U.S.C. 154(b) by 0 days.

(21) Appl. No.: 16/020,278

(22) Filed: Jun. 27, 2018

(65) Prior Publication Data
US 2019/0006783 A1    Jan. 3, 2019

(30) Foreign Application Priority Data

Jun. 28, 2017   (JP) ................................. 2017-126225
Feb. 26, 2018   (JP) ................................. 2018-032247

(51) Int. Cl.
| | |
|---|---|
| H01R 11/22 | (2006.01) |
| H01R 13/50 | (2006.01) |
| H01R 13/24 | (2006.01) |
| H01R 13/11 | (2006.01) |
| H01R 13/432 | (2006.01) |

(Continued)

(52) U.S. Cl.
CPC ........... *H01R 13/50* (2013.01); *H01R 13/111* (2013.01); *H01R 13/2457* (2013.01); *A61B 5/04286* (2013.01); *H01R 4/184* (2013.01); *H01R 13/432* (2013.01); *H01R 2201/12* (2013.01); *H01R 2201/20* (2013.01)

(58) Field of Classification Search
CPC H01R 13/113; H01R 13/2442; H01R 13/187; H01R 13/111; H01R 13/112; H01R 4/4809

USPC ....... 439/852, 862, 816, 851, 856, 857, 858, 439/861

See application file for complete search history.

(56) References Cited

U.S. PATENT DOCUMENTS

| | | | |
|---|---|---|---|
| 3,200,367 A | 8/1965 | Blanchenot | |
| 4,934,965 A * | 6/1990 | Buddrus | H01R 13/113 |
| | | | 439/845 |

(Continued)

FOREIGN PATENT DOCUMENTS

| | | |
|---|---|---|
| JP | 4996474 U | 8/1974 |
| JP | 2010073346 A | 4/2010 |

*Primary Examiner* — Phuong Chi T Nguyen
(74) *Attorney, Agent, or Firm* — The Webb Law Firm

(57) ABSTRACT

Provided is a connector including a connector terminal to which a mating terminal pin is connected and a connector housing configured to house the connector terminal therein. The connector housing has a tubular inner surface surrounding the connector terminal. The connector terminal includes elastic contact pieces arranged at intervals around a central axis of the tubular inner surface. Each elastic contact piece includes a contact portion extending along the central axis and being curved and a distal end portion located outward in a direction orthogonal to the central axis of the contact portion. The contact portion, when subjected to a pressing force from the mating terminal pin toward the tubular inner surface, is shaped into a flat form as a result of the distal end portion moving along the tubular inner surface. Also provided are an electric wire with the connector and a medical device sensor.

6 Claims, 12 Drawing Sheets

(51) Int. Cl.
*A61B 5/0428* (2006.01)
*H01R 4/18* (2006.01)

(56) References Cited

U.S. PATENT DOCUMENTS

| | | | | |
|---|---|---|---|---|
| 5,033,982 A | * | 7/1991 | Lucas | H01R 13/53 |
| | | | | 439/125 |
| 5,199,910 A | * | 4/1993 | Kahle | H01R 13/111 |
| | | | | 439/843 |
| 5,863,225 A | * | 1/1999 | Liebich | H01R 13/18 |
| | | | | 439/845 |
| 2002/0055297 A1 | * | 5/2002 | Feeny, Jr. | H01R 13/15 |
| | | | | 439/453 |
| 2003/0060090 A1 | * | 3/2003 | Allgood | H01R 11/289 |
| | | | | 439/845 |

* cited by examiner

CONNECTOR, ELECTRIC WIRE WITH CONNECTOR, AND MEDICAL DEVICE SENSOR

CROSS-REFERENCE TO RELATED APPLICATIONS

This application claims priority to Japanese Patent Application Nos. 2017-126225 and 2018-032247, filed Jun. 28, 2017, and Feb. 26, 2018, respectively, the disclosures of which are hereby incorporated in their entirety by reference.

FIELD OF THE INVENTION

The present invention relates to a connector that includes a connector terminal and a housing in which the connector terminal is housed, an electric wire with the connector, and a medical device sensor that includes the electric wire with the connector.

BACKGROUND OF THE INVENTION

Conventionally known is a connector terminal into and from which a mating terminal pin is inserted and removed (see Japanese Unexamined Utility Model Application Publication No. S49-96474). Specifically, as shown in FIG. 11, the connector terminal includes an electric connector 101 to which an electric wire 105 is connected, a lower contact piece 102 extending from the electric connector 101, and two upper contact pieces 103 continuously provided with a base portion of the lower contact piece 102 and extending in the same direction as that of the lower contact piece 102. These three contact pieces (i.e., the lower contact piece 102 and the two upper contact pieces 103) are arranged at intervals from each other in a circumferential direction of the mating terminal pin to be inserted. The contact pieces 102 and 103 are elastically deformable, and elastically deformed so that a clearance between each two adjacent leading ends thereof is widened by the mating terminal pin inserted from the leading ends side into a space surrounded by the three contact pieces 102 and 103. In the connector terminal 100, the mating terminal pin is retained by an elastic restoring force of the contact pieces 102, 103 (an elastic force for returning to the initial position). At this time, the contact pieces 102 and 103 retain the mating terminal pin while the contact pieces 102 and 103 on their leading end side in an inserting direction of the mating terminal pin are partially in contact with the mating terminal pin.

Connector terminals are required to have a retaining force so that the mating terminal pin is not pulled out of the connector terminal while in use. To obtain this retaining force, the abovementioned connector terminal 100 might, for example, have a smaller clearance between the leading ends of each adjacent contact pieces 102 and 103, that is, a smaller inscribed circle (see 8 in FIG. 12) tangent to the leading ends of the three contact pieces 102 and 103. The smaller clearance between the leading ends as above causes the mating terminal pin, which is in the state of being placed in the connector terminal 100, to be firmly retained by the elastic restoring force and thus less likely to be pulled out of the connector terminal 100.

In this case, however, a great resistance is caused when the mating terminal pin is inserted into the space surrounded by the three contact pieces 102 and 103; thus, the mating terminal pin is less likely to be all the way inserted.

SUMMARY OF THE INVENTION

It is therefore an object of the present invention to provide a connector into which the mating terminal pin is easily inserted and of which it is hardly pulled out, an electric wire with the connector, and a medical device sensor that includes the electric wire with the connector.

The following presents a simplified summary of the invention disclosed herein in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The connector according to the present invention includes: a connector terminal including a terminal base portion to which an electric wire is connectable, and an electric connector that extends from the terminal base portion and to which a mating terminal pin is detachably connected; and a connector housing including a terminal insertion portion through which the mating terminal pin P is insertable, and a terminal housing portion in which the connector terminal is housed in a state where the electric connector is directed to the terminal insertion port and held in engagement with the connector housing, the terminal housing portion including a tubular inner surface surrounding the electric connector, the electric connector including three or more flat plate-shaped elastic contact pieces arranged at intervals from each other around a central axis of the tubular inner surface inside the tubular inner surface, each of the three or more elastic contact pieces including: a contact portion that extends along the central axis and is curved to project toward the central axis, a base portion that extends from the contact portion toward the terminal base portion and is directly or indirectly connected to the terminal base portion; and a distal end portion that extends from an end portion opposite to the base portion of the contact portion and is positioned outward in a direction orthogonal to the central axis of the contact portion, and the contact portion being configured to be subjected to a pressing force from the mating terminal pin toward the tubular inner surface when the mating terminal pin is inserted through the terminal insertion port into the connector housing, and to be thereby elastically deformed from a curved form to a flat form so as to move a distal end edge of the distal end portion toward the terminal insertion port in a state where the distal end portion is held in contact with the tubular inner surface.

The connector may be configured such that the terminal housing portion has a projecting portion that projects from the tubular inner surface at a certain position in a direction of the central axis toward the central axis, and the certain position is located so that the distal end edge of the distal end portion abuts the projecting portion at the certain position when the contact portion is elastically deformed from the curved form to the flat form.

The connector may be configured such that the projecting portion is a wall portion that defines the terminal insertion port in the connector housing.

The connector may be configured such that the terminal housing portion has an elastic piece support configured to support the base portions of the elastic contact pieces from the outside in a direction orthogonal to the central axis.

An electric wire with a connector of the present invention includes: the connector according to any one of claims 1-4; and an electric wire connected to the terminal base portion of the connector.

A medical device sensor of the present invention includes: a medical sensor body; an output electric wire extending from the medical sensor body; and the connector according to any one of claims 1-4, wherein the output electric wire is connected to the terminal base portion of the connector.

BRIEF DESCRIPTION OF DRAWINGS

The foregoing and other features of the present invention will become apparent from the following description and drawings of an illustrative embodiment of the invention in which.

DETAILED DESCRIPTION OF THE PREFERRED EMBODIMENT

Hereinafter, an embodiment of a connector according to the present invention will be described with reference to FIG. 1 to FIG. 10.

Figure 1:
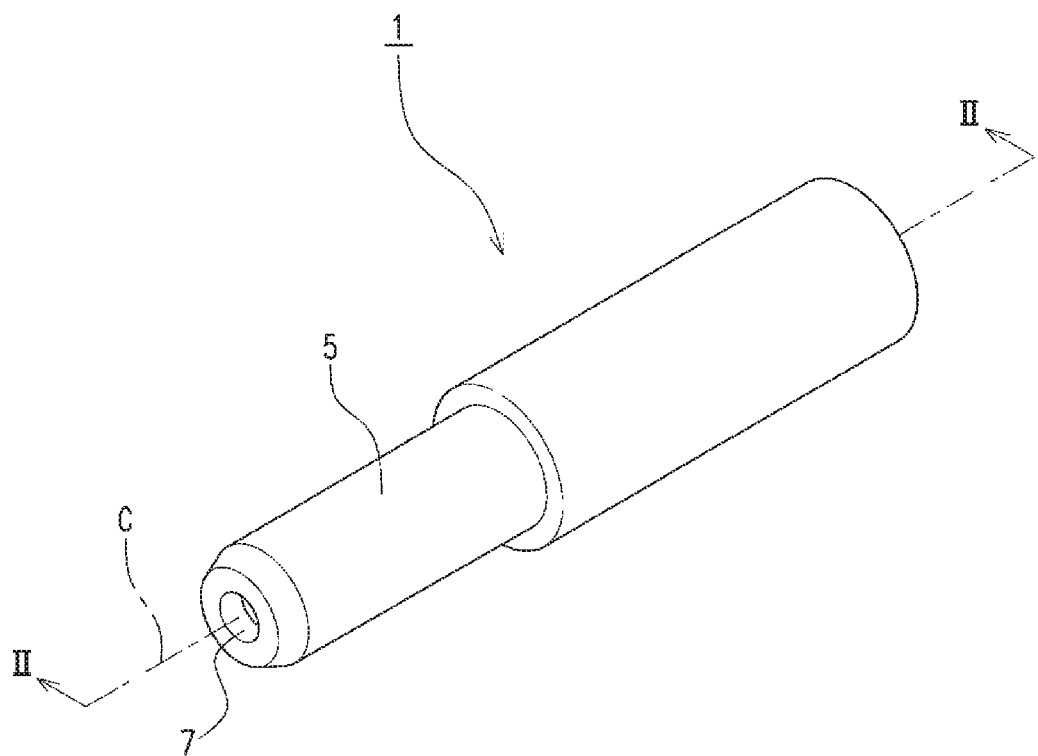
FIG. 1 is a perspective view of a connector according to one embodiment.
Figure 2:
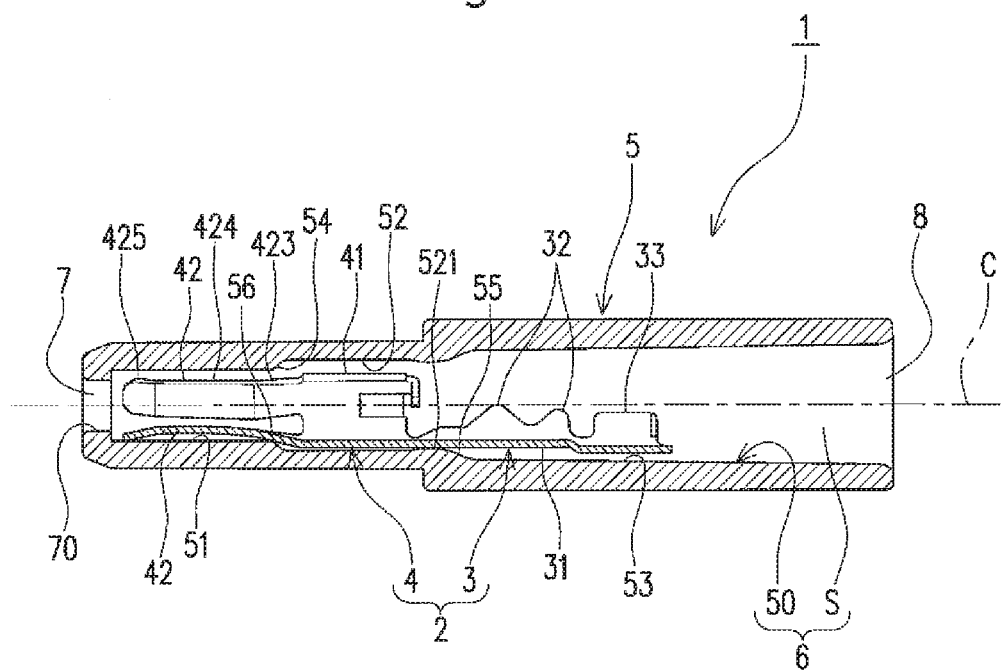
FIG. 2 is a cross sectional view taken along line II-II in FIG. 1.
Figure 3:
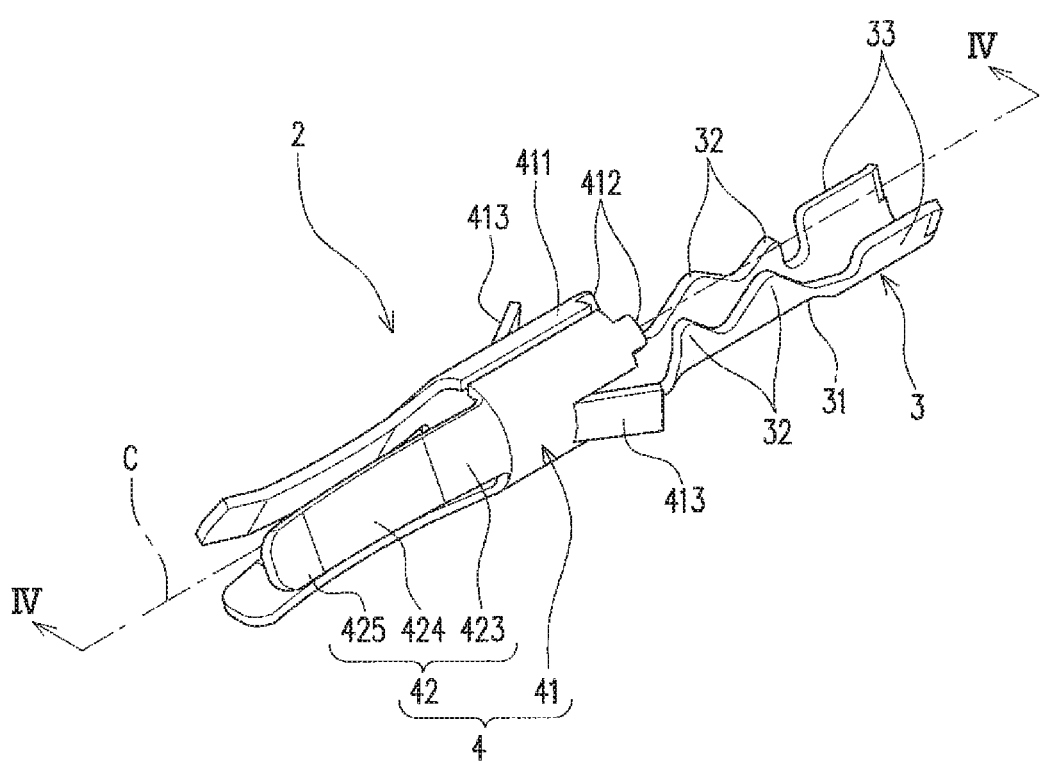
FIG. 3 is a perspective view of the a connector terminal used for the connector.
Figure 4:
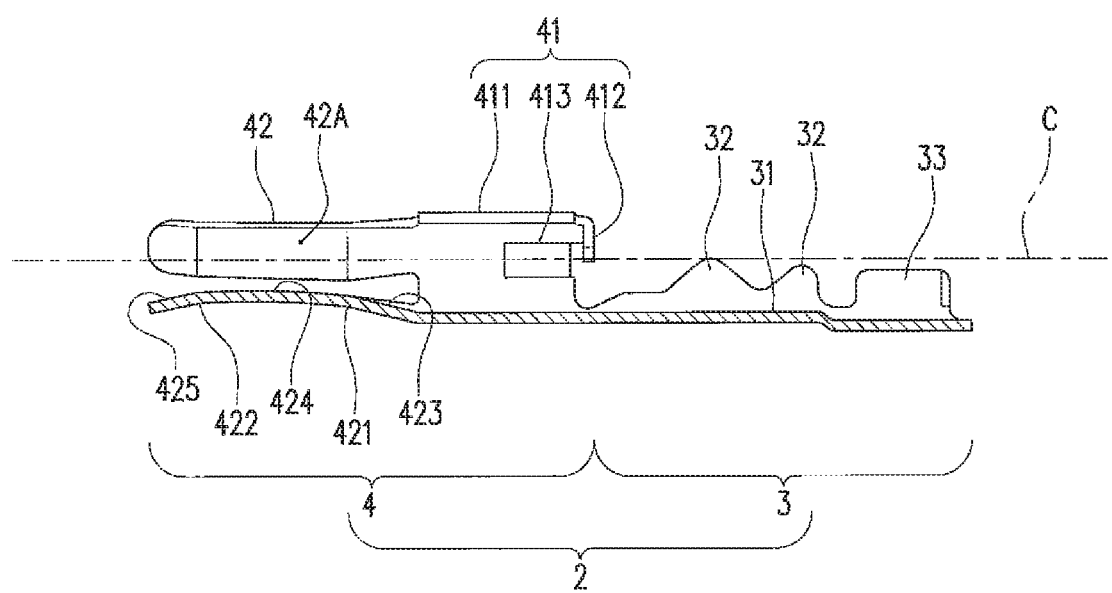
FIG. 4 is a cross sectional view taken along line IV-IV in FIG. 3.
Figure 5:
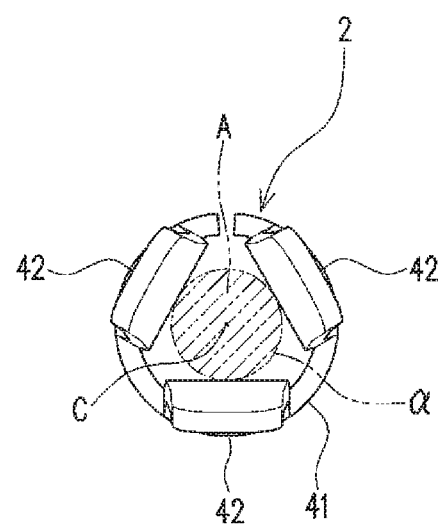
FIG. 5 is a schematic view of the connector terminal as seen from a distal end side in a direction of a central axis thereof.

As shown in FIG. 1 and FIG. 2, a connector 1 includes a connector terminal 2 to which an electric wire is connected, and a tubular connector housing 5 in which the connector terminal 2 is housed. The connector 1 is a female connector to which a mating terminal pin P (see FIG. 10) such as a male connector is connected (fitted).

As shown in FIG. 3 to FIG. 6, the connector terminal 2 includes a terminal base portion 3 to which an electric wire is connectable, and an electric connector 4 that extends from the terminal base portion 3 and to which the mating terminal pin P is detachably connected. The connector terminal 2 of this embodiment is formed of a conductive metal sheet that is stamped out into a specific shape (see FIG. 6) and then bent into a tubular shape with an axis parallel to a centerline C1 as a central axis C. The connector terminal 2 of this embodiment is formed of phosphor bronze, but may also be formed of brass, nickel silver, plated stainless steel, or the like. Hereinafter, in a direction of the central axis C, an electric connector 4 side (the left side in FIG. 2) is referred to as a distal end side, and a terminal base portion 3 side (the right side in FIG. 2) is referred to as a proximal end side.

The terminal base portion 3 includes a plate-shaped base body 31 extending in the direction of the central axis C, a plurality of conductive crimping pieces 32, and a pair of sheathed part crimping pieces 33 extending from a portion of the base body 31 closer to the proximal end side thereof than the conductive crimping pieces 32.

The conductive crimping pieces 32 are crimped to embrace a core wire (a conductor) exposed in a leading end portion of the electric wire so that the core wire is press-contacted to the base body 31, and the sheathed part crimping pieces 33 are configured to be crimped to have an insulation sheathed portion of the electric wire near the exposed core wire sandwiched between the base body 31 and the sheathed part crimping pieces 23.

Figure 6:
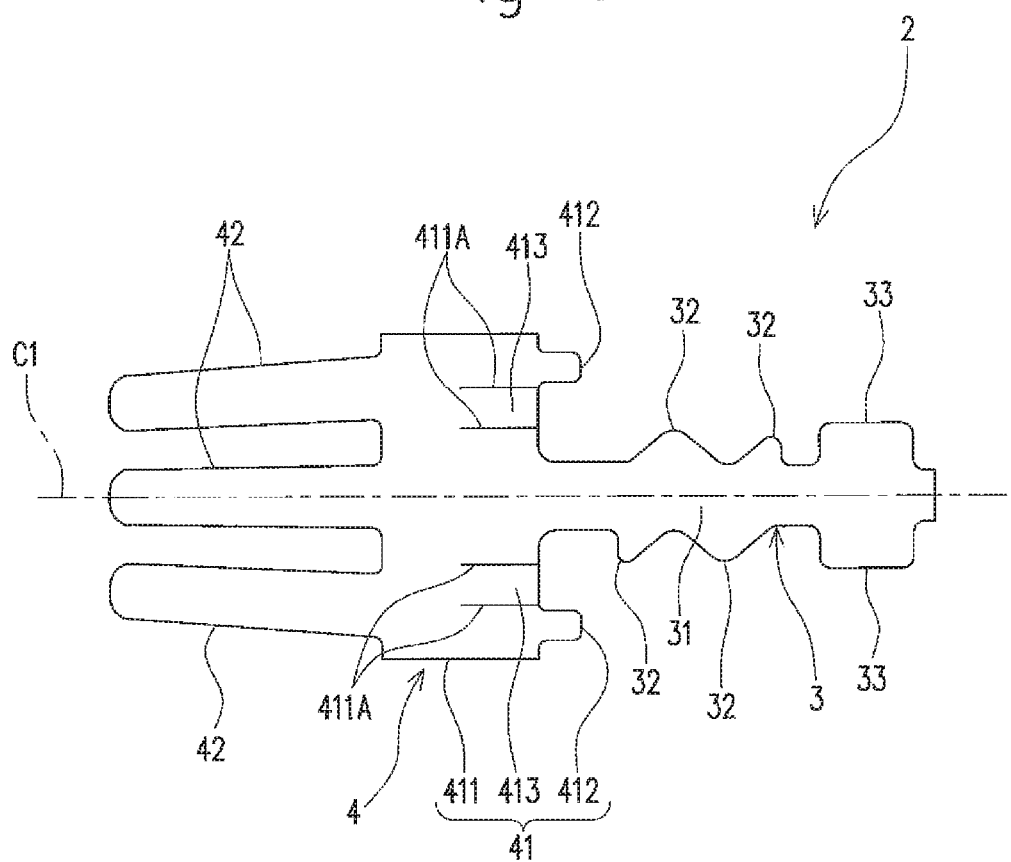
FIG. 6 is a development view of the connector terminal.

In the connector terminal 2 before it is bent as aforementioned (i.e., it is in the state shown in FIG. 6: hereinafter referred to as "flat plate-shaped connector terminal 2"), the plurality of conductive crimping pieces 32 extend from both sides in a width direction of the base body 31 (i.e., a direction orthogonal to the centerline C1: a vertical direction in FIG. 6) toward the outside thereof in the width direction. In the connector terminal 2 of this embodiment, the conductive crimping pieces 32 on one side in the width direction (i.e., the upper side in FIG. 6) and the conductive crimping pieces 32 on the other side (i.e., the lower side in FIG. 6) alternately extend while being displaced from each other in the direction of the centerline C1 (i.e., they are alternately arranged).

In the base body 31 of the flat plate-shaped connector terminal 2, the pair of sheathed part crimping pieces 33 respectively extend toward the outside in the width direction from portions adjacent to the conductive crimping pieces 32 on the proximal end side thereof in the direction of the centerline C1. The sheathed part crimping piece 33 on the one side in the width direction and the sheathed part crimping piece 33 on the other side therein are both located at the same position with respect to the direction of the centerline C1.

The base body 31 is bent to be curved so that the terminal base portion 3 is formed from a part of the flat plate-shaped connector terminal 2 that includes the base body 31, the conductive crimping pieces 32, and the sheathed part crimping pieces 33.

The electric connector 4 includes a connector body 41 continuously provided with the base body 31, and three or more elastic contact pieces 42 arranged at intervals around the central axis C. The electric connector 4 is conductively connected (fitted) to the mating terminal pin P (see FIG. 10) when the mating terminal pin P is inserted into an area A (see FIG. 5) surrounded by the three or more elastic contact pieces 42. In this embodiment, there are three elastic contact pieces 42.

A connector body 41 includes a tubular portion 411 surrounding the central axis C, a stopper piece 412 extending from the proximal end of the tubular portion 411 toward the central axis C, and terminal side engagement portions 413 that extend outward from the tubular portion 411 and engage with the connector housing 5.

Figure 10:
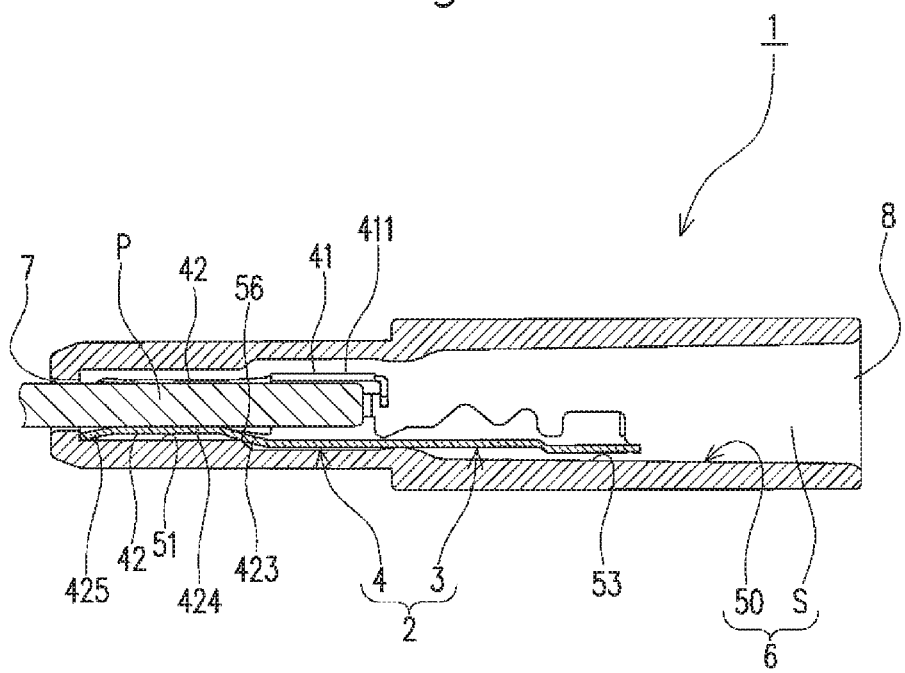
FIG. 10 is a cross sectional view showing a state where the connector and the mating terminal pin are fitted to each other.
Figure 11:
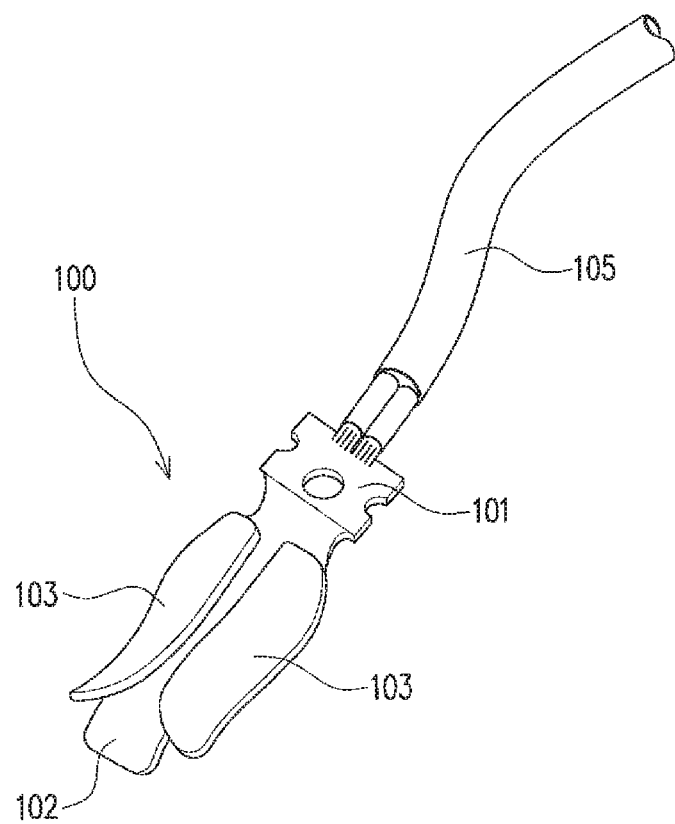
FIG. 11 is an explanatory view for a conventional connector terminal.
Figure 12:
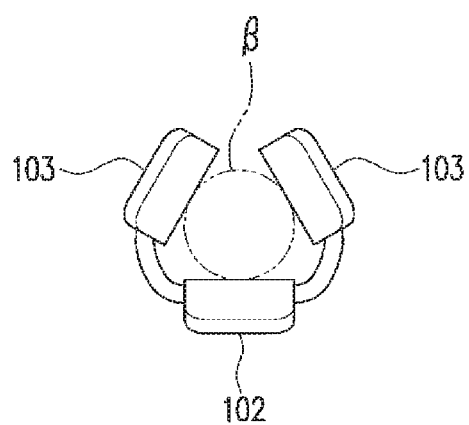
FIG. 12 is a schematic view of the connector terminal as seen from a distal end side in a direction of a central axis thereof.

The tubular portion 411 is a portion inside which a leading end portion of the mating terminal pin P is positioned (i.e. the area surrounded by the tubular portion 411) when the mating terminal pin P is fitted to the connector 1 (see FIG. 10). The tubular portion 411 is formed with a rectangular plate portion of the flat plate-shaped connector terminal 2 having a shape elongated in a direction orthogonal to the centerline C1, the rectangular plate portion being entirely curved into a tubular shape so as to make the central axis C as the center and having the edges in its longitudinal direction of the rectangular plate portion opposed to each other.

The stopper piece 412 is configured to stop the leading end of the mating terminal pin P, when the mating terminal pin P is fitted to the connector 1, from moving further into the inside of the connector 1 (toward the proximal end of the connector 1). That is, the stopper piece 412 is configured to abut the leading end of the mating terminal pin P when the mating terminal pin P moving along the central axis C enters the tubular portion 411 to thereby prevent the leading end of the mating terminal pin P from moving further into the inside of the connector 1.

The stopper piece 412 is formed with a portion extending in the direction of the centerline C1 from the proximal end edge of the tubular portion 411 in the flat plate-shaped connector terminal 2 shown in FIG. 6, the portion being bent toward the central axis C in the state where the tubular portion 411 is in a tubular shape. In the electric connector 4 of this embodiment, a plurality of (two in this embodiment) stopper pieces 412 are arranged at intervals in a circumferential direction of the tubular portion 411.

The terminal side engagement portions 413 are configured to engage with an engagement portion (a housing side engagement portion 521 to be described later: see FIG. 2) provided inside the connector housing 5 when the connector terminal 2 is inserted through a proximal end opening 8 (see FIG. 2) into the inside of the connector housing 5 and moves to a specific position. This configuration allows the connector terminal 2 to be locked in the connector housing 5 and consequently prevented from moving to the proximal end side inside the connector housing 5.

Specifically, the terminal side engagement portions 413 project from the tubular portion 411 and are inclined with respect to the central axis C so as to be away from the central axis C as they advance toward the proximal end. Each of the terminal side engagement portions 413 is formed with a portion between a pair of cut lines 411A (see FIG. 6) that extend from a proximal end edge of the tubular part 411 of the flat plate-shaped connector terminal 2 toward a distal end edge thereof and are provided at an interval from each other in a direction orthogonal to the centerline C1, the portion being raised outward.

The three elastic contact pieces 42 extend along the central axis C, are pressed by the mating terminal pin P that is inserted through a terminal insertion port 7 (see FIG. 2) of the connector housing 5, and are thereby elastically deformed. The elastic contact pieces 42 are arranged at intervals from each other on the circumference of a circle with the central axis C as the center. A specific configuration of each of the elastic contact pieces 42 is described as follows.

The elastic contact pieces 42 are elastically-deformable plate-shaped portions that extend from the connector body 41 toward the distal end. The elastic contact pieces 42 are arranged at equal intervals around the central axis C, with a main surface (a surface orthogonal to a thickness direction thereof) 42A (see FIG. 4) directed to the central axis C. Each of the elastic contact pieces 42 has two bent portions (a first bent portion 421 and a second bent portion 422) arranged at an interval from each other in the direction of the central axis C. Hereinafter, a portion of the elastic contact piece 42 on the proximal end side of the first bent portion 421 is referred to as a base portion 423, a portion thereof between the first bent portion 421 and the second bent portion 422 is referred to as a contact portion 424, and a portion thereof on the distal end side of the second bent portion 422 is referred to as a distal end portion 425.

The base portion 423 extends from the contact portion 424 toward the terminal base portion 3, and is directly or indirectly connected to the terminal base portion 3. The base portion 423 of this embodiment is connected to the terminal base portion 3 through the connector body 41. The base portion 423 connects the contact portion 424 with the connector body 41 (specifically, the tubular portion 411) and thereby restricts the contact portion 424 from moving toward the terminal base portion 3. The base portion 423 is inclined with respect to the central axis C so as to be away from the central axis C as it advances from the contact portion 424 toward the proximal end (see FIG. 2 and FIG. 4). The base portion 423 of this embodiment abuts the connector housing 5 at an intermediate position in its longitudinal direction (see FIG. 2).

Figure 7:
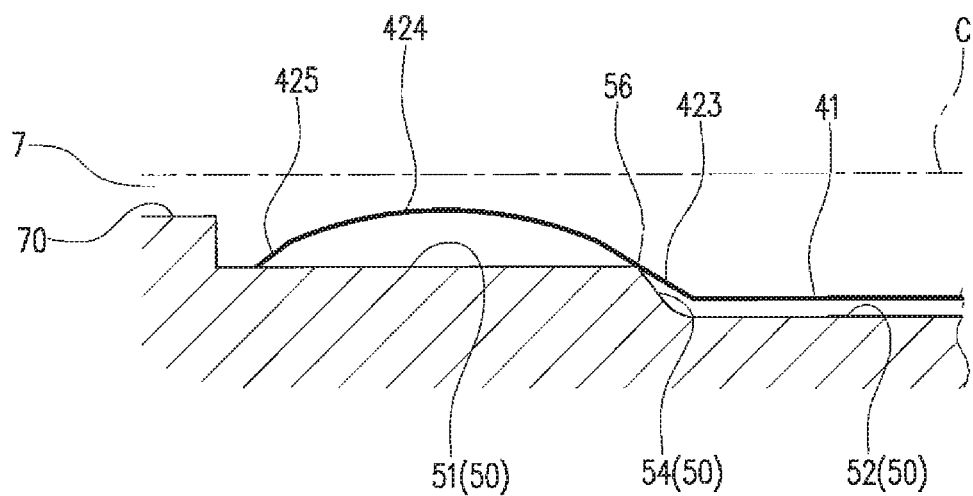
FIG. 7 is a schematic explanatory view for an elastic contact piece.
Figure 8:
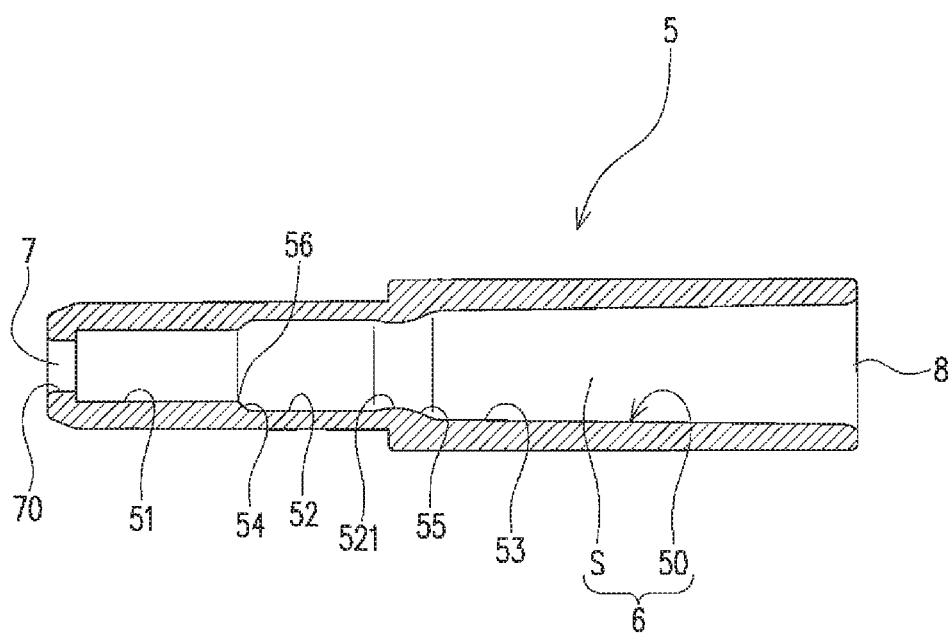
FIG. 8 is a cross sectional view of a connector housing used for the connector.

The contact portion 424 is a portion that is in contact (conduction) with the mating terminal pin P when the mating terminal pin P is inserted through the terminal insertion port 7. The contact portion 424 is deflectable. Specifically, the contact portion 424 extends along the central axis C and is curved in such a direction as to project toward the central axis C. With this curving, an inscribed circle a (see FIG. 5) that is centered at the central axis C and tangent to a portion of each of the contact portions 424 closest to the central axis C is made smaller than the outer circumference of the mating terminal pin P. This configuration causes the contact portions 424 to be pressed in a direction away from the central axis C by the mating terminal pin P that is inserted into the area A surrounded by the elastic contact pieces 42, and to be thereby elastically deformed (from a curved form to a flat form). The contact portion 424 of this embodiment is provided so that its proximal end is closer to the central axis C than its distal end. Note that the actual curving (deflection) of the contact portion 424 is so small that the schematic view in FIG. 7 shows the exaggerated curving (deflection) of the contact portion 424.

The distal end portion 425 extends from a distal end of the contact portion 424 (the edge on the opposite side to the base portion 423) and is positioned outward of the contact portion 424 in a direction orthogonal to the central axis C. Specifically, the distal end portion 425 is inclined with respect to the central axis C so as to be away from the central axis C as it advances from the contact portion 424 toward the distal end (see FIG. 2, FIG. 4, and FIG. 7). The distal end portion 425 is configured to have its leading end moving toward the distal end while being in contact with an inner surface 50 (specifically, a first portion 51: see FIG. 7), that is, sliding toward the distal end with respect to the inner surface 50 of the connector housing 5, as the mating terminal pin P is inserted through the terminal insertion port 7 of the connector housing 5 to elastically deform the contact portion 424.

The connector terminal 2 configured as above is housed in the connector housing 5 with the electric connector 4 directed to the terminal insertion port 7 (see FIG. 2).

As shown in FIG. 1, FIG. 2, FIG. 7, and FIG. 8, the connector housing 5 includes a terminal housing portion 6 in which the connector terminal 2 is housed, and the terminal insertion port 7 through which the mating terminal pin P is inserted. The connector housing 5 also has the proximal end opening 8 through which the connector terminal 2 is inserted. A more specific description is provided below.

The connector housing 5 has a tubular shape having the central axis C, and is formed of an insulating resin. The connector housing 5 has an inner surface 50. The inner surface 50 defines a space (a housing space) S in which the connector terminal 2 is housed. The terminal housing portion 6 of this embodiment has the inner surface 50 and the housing space S. The terminal insertion port 7 is configured to communicate the housing space S with the outside in the direction of the central axis C at the distal end of the connector housing 5, and the proximal end opening 8 is configured to communicate the housing space S with the outside in the direction of the central axis C at the proximal end of the connector housing 5.

The inner surface 50 of this embodiment defines a circular or substantially circular cross section at every position in the direction of the central axis C (cross section in a surface direction orthogonal to the central axis C of the inner surface 50). The inner surface 50 defines a plurality of portions having different diameters. Specifically, the inner surface 50 has, in order from the distal end side to the proximal end side, the first portion 51 having a smallest diameter, a second portion 52 having a greater diameter than the first portion 51, and a third portion 53 having a greater diameter than the second portion 52 (having a greatest diameter). The first portion 51 and the second portion 52 are connected to each other through a first reduced diameter portion 54 that has a diameter reduced as it advances toward the distal end. The second portion 52 and the third portion 53 are connected to each other through a second reduced diameter portion 55 that has a diameter reduced as it advances toward the distal end. The portions 51 to 55 that are defined by the inner surface 50 share the same central axis.

The first portion 51, the first reduced diameter portion 54, and the second portion 52 are configured to enclose the electric connector 4 through the inner surface 50. The second portion 52 has a housing side engagement portion 521 configured to engage with the terminal side engagement portions 413 at a position corresponding to the terminal side engagement portions 413 of the electric connector 4 (specifically, the connector body 41). The housing side engagement portion 521 of this embodiment is defined by partial reduction of the diameter of the inner surface 50, which is provided in the direction of the central axis C, that is, a portion projecting toward the central axis C, and is provided at a position adjacent to (continuous with) the second reduced diameter portion 55 in the direction of the central axis C. A boundary portion (elastic piece support) 56 between the first portion 51 and the first reduced diameter portion 54 abuts the base portions 423 of the elastic contact pieces 42 from the outside thereof (specifically, the outside in the radial direction of the inner surface 50). That is, the boundary portion 56 supports the base portions 423 from the outside.

The proximal end portion of the third portion 53 defines the proximal end opening 8 that is formed in the proximal end portion of the connector housing 5. The housing space S of the connector housing 5 and the outside space communicate with each other through the proximal end opening 8.

The connector housing 5 has a projecting portion 70 that projects from the first portion 51 at a certain position in the direction of the central axis C toward the central axis C. The projecting portion 70 of this embodiment is a wall portion (a distal end wall portion) that defines the terminal insertion port 7 at the distal end of the connector housing 5. That is, the projecting portion 70 projects from the end edge on the distal end side of the first portion 51 toward the central axis C. The projecting portion 70 is provided at a position at which it abuts the distal end portions 425 when the contact portions 424 are elastically deformed in the direction of the central axis C from the curved form to the flat form. The housing space S of the connector housing 5 and the outside space communicate with each other through the terminal insertion port 7.

The connector 1 configured as above is used by, for example, being connected to the leading end of the electric wire. Specifically, the connector 1 is connected to the electric wire as follows.

First, the electric wire is connected to the terminal base portion 3 of the connector terminal 2. Specifically, an end portion of the electric wire with its core wire exposed is placed on the base body 31 of the terminal base portion 3, and then the conductive crimping pieces 32 are crimped to embrace the core wire. The core wire is thereby press-contacted to the base body 31. Further, the sheathed part crimping pieces 33 are crimped. Consequently, an insulation sheathed portion of the electric wire is sandwiched between the base body 31 and the sheathed part crimping pieces 33.

When the connector terminal 2 is connected to the end portion of the electric wire, the connector terminal 2 to which the electric wire is connected is inserted into the terminal housing portion 6 (i.e., inside the housing space 5) through the proximal end opening 8 of the connector housing 5, while having the electric connector 4 being directed to the terminal insertion port 7 side. At this time, the connector terminal 2 is pushed to the distal end side (i.e., the terminal insertion port 7 side) until the terminal side engagement portions 413 of the electric connector 4 (specifically, an end edge on the free end side of the terminal side engagement portion 413) pass the housing side engagement portion 521 of the inner surface 50. The connection (mounting) of the connector 1 to the electric wire is thus completed when the terminal side engagement portions 413 engage with the housing side engagement portion 521.

Figure 9:
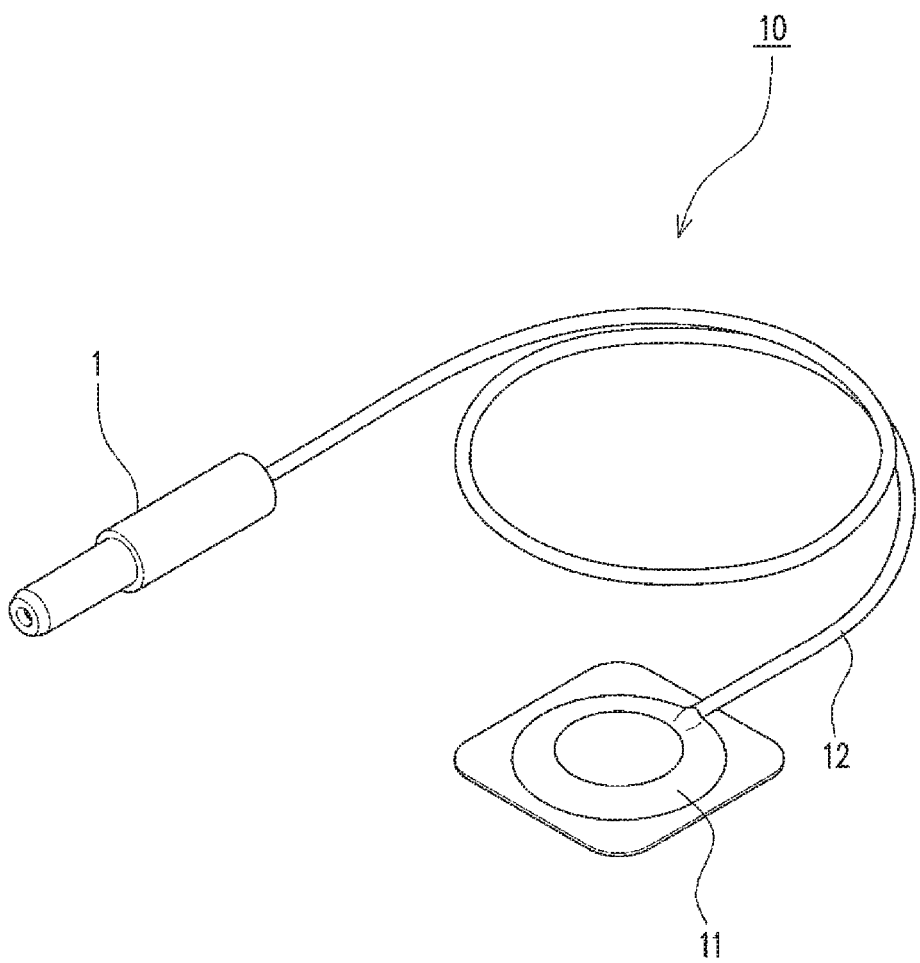
FIG. 9 is an explanatory view for a medical device sensor.

The connector 1 may also be used, for example, for medical device sensors or the like. The medical device sensor of this embodiment is, for example, an electrocardiographic electrode 10 as shown in FIG. 9. The electrocardiographic electrode 10 includes an electrode body 11 that is attached to, for example, the skin of a chest of a medical examinee or the like, an output electric wire 12 extending from the electrode body 11, and the connector 1 connected to a leading end of the output electric wire 12.

According to the connector 1 configured as above, the base portion 423 and the distal end portion 425 of each of the elastic contact pieces 42 that are restricted from moving in a direction orthogonal to the central axis C (i.e., a direction in which the elastic contact piece 42 is pressed by the mating terminal pin P) are configured to support both ends of the contact portion 424. Thus, the contact portion 424 is elastically deformed to have the flat form to conform to the mating terminal pin P that has been inserted to the innermost position through the terminal insertion port 7. A specific description is provided below.

In the state before the mating terminal pin P is inserted (the initial state), the contact portion 424 of each of the elastic contact pieces 42 is curved to project toward the central axis C, as shown in FIG. 7. When the mating terminal pin P is inserted through the terminal insertion port 7 in the direction of the central axis C in this state, the mating terminal pin P, as it advances toward the proximal end, presses the contact portions 424 of the elastic contact pieces 42 radially outward of the inner surface 50, since the inscribed circle a (see FIG. 5) is smaller than the outer circumference of the mating terminal pin P. That is, the contact portions 424 of the elastic contact pieces 42 are subjected to a pressing force of the mating terminal pin P exerted radially outward of the inner surface 50.

At this time, the proximal ends of the contact portions 424 are restricted from moving since they are connected to the base portions 423 that extend from the connector body 41 engaging with the connector housing 5 and that are supported by the boundary portion 56 from the outside in the radial direction of the inner surface 50. Thus, the distal end edges of the contact portions 424 subjected to the pressing force move toward the terminal insertion port 7, which thereby elastically deforms the contact portions 424 to make their curvature small. When the mating terminal pin P is fully inserted, the contact portions 424 are deformed to the flat form along the mating terminal pin P (see FIG. 10).

When the contact portions 424 are elastically deformed to be straightened, the distal end portions 425 are restricted by the first portion 51 from moving radially outward of the inner surface 50, but move toward the distal end (i.e., the terminal insertion port 7) while being in contact with the first portion 51 since they are capable of moving along the first portion 51. That is, the distal end portions 425 slide (move while sliding) toward the terminal insertion port 7 along the first portion 51. When the contact portions 424 are elastically deformed to have the flat form to conform to the mating terminal pin P, the distal end portions 425 having slid toward the terminal insertion port 7 along the first portion 51 abut the projecting portion 70 (see FIG. 10). In the state where the contact portions 424 have been elastically deformed to be straightened as aforementioned, the entire areas of the contact portions 424 in the direction of the central axis C are in contact with the mating terminal pin P.

As a result, in the connector 1, a sufficient force for retaining the mating terminal pin P is obtained by a retaining force resulting from an elastic restoring force of the elastic contact pieces 42 (the pressing force applied to the mating terminal pin P) and a frictional force resulting from the contact between the contact portions 424 and the mating terminal pin P through the entire areas of the contact portions 424 in the direction of the central axis C, that is, in the insertion direction (force against the mating terminal pin P that is being pulled out). In addition, the connector 1 configured as above requires a smaller elastic restoring force (the pressing force of the elastic contact pieces 42 applied to the mating terminal pin P) than in the case where a force for retaining the mating terminal pin P is obtained only by the elastic restoring force. This enables ease of inserting the mating terminal pin P into the connector.

That is, while a mating terminal pin is hard to be inserted into a connector that is configured to obtain a force for retaining the mating terminal pin using only the elastic restoring force of elastic contact pieces, the connector 1 of this embodiment is configured to obtain the force for retaining the mating terminal pin P using the frictional force in addition to the elastic restoring force, which, as a result, enables both ease of inserting the mating terminal pin P into the connector and obtaining a sufficient force for retaining the mating terminal pin P that has been inserted.

In the connector 1 of this embodiment, the inner surface 50 has the projecting portion 70 that projects from the first portion 51 at a certain position (in this embodiment, the distal end of the first portion 51) in the direction of the central axis C toward the central axis C. The projecting portion 70 is provided at a position at which it abuts the distal end portions 425 when the contact portions 424 are elastically deformed from the curved form to the flat form. That is, a clearance between the projecting portion 70 and the distal end portion 425 of each of the elastic contact pieces 42 in the initial state (i.e., the state where the mating terminal pin P is not inserted) is set to such a dimension that the distal end portion 425 abuts the projecting portion 70 at the timing when the corresponding curved contact portion 424, subjected to the pressing force of the mating terminal pin P toward the inner surface 50, is elastically deformed from the curved form to the flat form.

According to such a configuration, the distal end portions 425 of the elastic contact pieces 42 abut the projecting portion 70 to restrict the distal end portions 425 from moving further toward the terminal insertion port 7 when the contact portions 424 are elastically deformed to the flat form by the inserted mating terminal pin P. This configuration can suppress the elastic restoring force of the contact portions 424 from being partially directed toward the terminal insertion port 7. As a result, the pressing force of the elastic contact pieces 42 is effectively applied to the mating terminal pin P. That is, in the state where the distal end portions 425 are not restricted from moving toward the terminal insertion port 7, the elastic restoring force generated by the contact portions 424 having been deformed to have the flat form could be partially directed through the distal end portions 425; however, the force directed theretrhough is suppressed when the distal end portions 425 abut the projecting portion 70, which results in efficient application of the elastic restoring force of the contact portions 424 to the mating terminal pin P.

In the connector 1 of this embodiment, the projecting portion 70 is a wall portion that defines the terminal insertion port 7 at the distal end of the connector housing 5. This configuration can downsize the connector 1 compared to a connector having the configuration in which the wall portion that defines the terminal insertion port 7 is provided separately from the projecting portion 70.

In the connector 1 of this embodiment, the inner surface 50 of the connector housing 5 has the boundary portion 56 that supports the base portions 423 of the elastic contact pieces 42 from the outside. This boundary portion 56 supports the base portions 423 of the elastic contact pieces 42 and further restricts the contact portions 424 from moving. Thus, the elastic restoring force generated in the contact portions 424 by elastic deformation is suppressed from being partially directed through the base portions 423. Consequently, the pressing force resulting from the elastic restoring force generated in the contact portions 424 of the elastic contact pieces 42 is more efficiently applied to the mating terminal pin P.

In the electric wire to which the connector 1 configured as above is connected (i.e., the electric wire with the connector), the mating terminal pin P is easily inserted into the connector 1, and the inserted mating terminal pin P is hardly pulled out.

That is, the medical device sensor 10 for which the connector 1 is used allows the mating terminal pin P to be easily inserted into the connector 1 and the inserted mating terminal pin P to be hardly pulled out.

It is a matter of course that the connector, the electric wire with the connector, and the medical device sensor of the present invention are not limited to the aforementioned embodiment, but various modifications can be made without departing from the gist of the present invention. For example, a configuration of an embodiment may be added to a configuration of another embodiment, and part of a configuration of an embodiment may be replaced by a configuration of another embodiment. Further, part of a configuration of an embodiment may be deleted.

The connector 1 of the aforementioned embodiment includes three elastic contact pieces 42, without limitation thereto. There may be the case where four or more elastic contact pieces 42 are included. Even in this case, the plurality of elastic contact pieces 42 may be arranged at intervals from each other around the central axis C, with their main surfaces 42A directed to the central axis C, that is, arranged at intervals from each other on the circumference of a circle with the central axis C as the center.

In the connector 1 of the aforementioned embodiment, the projecting portion 70 defines the wall portion at the distal end of the connector housing 5 (i.e., the wall portion at which the terminal insertion port 7 is provided), that is, the wall portion at the distal end serves also as the projecting portion 70, without limitation thereto. The wall portion at the distal end may be provided separately from the projecting portion 70.

In the connector 1 of the aforementioned embodiment, the inner surface 50 of the connector housing 5 (specifically, the first portion 51) has the projecting portion 70 configured such that the distal end portions 425 abut the projecting portion 70 when the contact portions 424 are elastically deformed to be straightened, without limitation thereto. The inner surface 50 may be configured without the projecting portion 70. Even according to such a configuration, the contact portions 424 are elastically deformed to have the flat form to conform to the mating terminal pin P that has been inserted to the innermost position through the terminal insertion port 7. As a result, a sufficient force for retaining the mating terminal pin P is obtained by a retaining force resulting from the elastic restoring force of the elastic contact pieces 42 and a frictional force resulting from the contact between each of the contact portions 424 and the mating terminal pin P through the entire area of each of the contact portions 424 in the direction of the central axis C. In addition, the connector 1 configured as above requires a smaller elastic restoring force (the pressing force of the elastic contact pieces 42 applied to the mating terminal pin P) than in the case where a force for retaining a mating terminal pin is obtained only by the elastic restoring force, which enables ease of insertion of the mating terminal pin P into the connector 1.

In the connector 1 of the aforementioned embodiment, the elastic contact pieces 42 have a flat plate shape and are elastically deformable as a whole, without limitation thereto. In the elastic contact pieces 42, at least the contact portions 424 may be elastically deformable. According to such a configuration, the contact portions 424 are elastically deformed from the curved form to the flat form to conform to the mating terminal pin P that has been inserted to the innermost position through the terminal insertion port 7.

In the connector 1 of the aforementioned embodiment, the base portions 423 of the elastic contact pieces 42 are supported by or held in abutting engagement with the boundary portion 56 of the inner surface 50, without limitation thereto. The base portions 423 of the elastic contact pieces 42 do not have to be in contact with the inner surface 50.

The connector housing 5 of the aforementioned embodiment has a tubular shape, without limitation thereto. The connector housing 5 may have any outer configuration as long as it has the inner surface 50 (i.e., the terminal housing portion 6).

The connector housing 5 of the aforementioned embodiment includes one inner surface 50 (i.e., one terminal housing portion 6), without limitation thereto. The connector housing 5 may include a plurality of inner surfaces 50 (i.e., a plurality of terminal housing portions 6). In this case, the connector has a plurality of connector terminals 2, the number of which is equal to or less than the number of the inner surfaces 50.

A specific configuration of the terminal base portion 3 of the connector terminal 2 is not limited to the aforementioned embodiment. The terminal base portion 3 of the connector terminal 2 of the aforementioned embodiment is configured so that the electric wire is connected by crimping, but may be configured so that the electric wire is connected by, for example, soldering or other connection methods. Further, a specific configuration of the conductive crimping pieces 32 and the sheathed part crimping pieces 33 is not limited to the aforementioned embodiment, either.

A specific configuration of the electric wire connected to the connecter terminal 2 is not limited to the aforementioned embodiment, either. The core wire of the electric wire may be a metal core wire, or may be a core wire formed of, for example, conductive fibers such as plated fibers or carbon fibers.

The medical device sensor of the aforementioned embodiment is an electrocardiographic electrode, without limitation thereto. The medical device sensor may be, for example, a blood pressure sensor, an SpO2 (arterial oxygen saturation) sensor, an expiration sensor, and the like.

The connector 1 is connectable to an electric wire that is used for a variety of devices, not limited to the medical device sensor.

The connector, the electric wire with the connector, and the medical device sensor of this embodiment are as described above, but the present invention is not limited to the aforementioned embodiment, and the design can be appropriately modified within the scope intended by the present invention. The operational advantages of the present invention are also not limited to the foregoing embodiments. That is, the embodiments disclosed herein should be construed in all respects as illustrative but not limiting. The scope of the present invention is not indicated by the foregoing description but by the scope of the claims. Further, the scope of the present invention is intended to include all the modifications equivalent in the sense and the scope of the claims.

What is claimed is:

1. An electric wire connector, comprising:
    a connector terminal comprising a terminal base portion to which the electric wire is connectable, and an electric connector that extends from the terminal base portion and to which a mating terminal pin is detachably connected; and
    a connector housing comprising a terminal insertion portion through which the mating terminal pin P is insertable, and a terminal housing portion in which the connector terminal is housed in a state where the electric connector is directed to the terminal insertion port and held in engagement with the connector housing,
    the terminal housing portion comprising a tubular inner surface surrounding the electric connector,
    the electric connector comprising three or more flat plate-shaped elastic contact pieces arranged at intervals from each other around a central axis of the tubular inner surface inside the tubular inner surface,
    each of the three or more elastic contact pieces comprising: a contact portion that extends along the central axis and is curved to project toward the central axis, a base portion that extends from the contact portion toward the terminal base portion and is directly or indirectly connected to the terminal base portion; and a distal end portion that extends from an end portion opposite to the base portion of the contact portion and is positioned outward in a direction orthogonal to the central axis of the contact portion, and the contact portion being configured to be subjected to a pressing force from the mating terminal pin toward the tubular inner surface when the mating terminal pin is inserted through the terminal insertion port into the connector housing, and to be thereby elastically deformed from a curved form to a flat form so as to move a distal end edge of the distal end portion toward the terminal insertion port in a state where the distal end portion is held in contact with the tubular inner surface.

2. The electric wire connector according to claim 1, wherein
the terminal housing portion has an elastic piece support configured to support the base portions of the elastic contact pieces from the outside in a direction orthogonal to the central axis.

3. The electric wire connector according to claim 1, wherein
the terminal housing portion has a projecting portion that projects from the tubular inner surface at a certain position in a direction of the central axis toward the central axis, and
the certain position is located so that the distal end edge of the distal end portion abuts the projecting portion at the certain position when the contact portion is elastically deformed from the curved form to the flat form.

4. The electric wire connector according to claim 3, wherein
the projecting portion is a wall portion that defines the terminal insertion port in the connector housing.

5. An electric wire with an electric wire connector, comprising:
a connector terminal comprising a terminal base portion to which the electric wire is connectable, and an electric connector that extends from the terminal base portion and to which a mating terminal pin is detachably connected; and
a connector housing comprising a terminal insertion portion through which the mating terminal pin P is insertable, and a terminal housing portion in which the connector terminal is housed in a state where the electric connector is directed to the terminal insertion port and held in engagement with the connector housing,
the terminal housing portion comprising a tubular inner surface surrounding the electric connector,
the electric connector comprising three or more flat plate-shaped elastic contact pieces arranged at intervals from each other around a central axis of the tubular inner surface inside the tubular inner surface,
each of the three or more elastic contact pieces comprising: a contact portion that extends along the central axis and is curved to project toward the central axis, a base portion that extends from the contact portion toward the terminal base portion and is directly or indirectly connected to the terminal base portion; and a distal end portion that extends from an end portion opposite to the base portion of the contact portion and is positioned outward in a direction orthogonal to the central axis of the contact portion, and
the contact portion being configured to be subjected to a pressing force from the mating terminal pin toward the tubular inner surface when the mating terminal pin is inserted through the terminal insertion port into the connector housing, and to be thereby elastically deformed from a curved form to a flat form so as to move a distal end edge of the distal end portion toward the terminal insertion port in a state where the distal end portion is held in contact with the tubular inner surface; and
the electric wire connected to the terminal base portion of the electric wire connector.

6. A medical device sensor, comprising:
a medical sensor body; an output electric wire extending from the medical sensor body; and an electric wire connector comprising:
a connector terminal comprising a terminal base portion to which the output electric wire is connectable, and an electric connector that extends from the terminal base portion and to which a mating terminal pin is detachably connected; and
a connector housing comprising a terminal insertion portion through which the mating terminal pin P is insertable, and a terminal housing portion in which the connector terminal is housed in a state where the electric connector is directed to the terminal insertion port and held in engagement with the connector housing,
the terminal housing portion comprising a tubular inner surface surrounding the electric connector,
the electric connector comprising three or more flat plate-shaped elastic contact pieces arranged at intervals from each other around a central axis of the tubular inner surface inside the tubular inner surface,
each of the three or more elastic contact pieces comprising: a contact portion that extends along the central axis and is curved to project toward the central axis, a base portion that extends from the contact portion toward the terminal base portion and is directly or indirectly connected to the terminal base portion; and a distal end portion that extends from an end portion opposite to the base portion of the contact portion and is positioned outward in a direction orthogonal to the central axis of the contact portion, and
the contact portion being configured to be subjected to a pressing force from the mating terminal pin toward the tubular inner surface when the mating terminal pin is inserted through the terminal insertion port into the connector housing, and to be thereby elastically deformed from a curved form to a flat form so as to move a distal end edge of the distal end portion toward the terminal insertion port in a state where the distal end portion is held in contact with the tubular inner surface, wherein
the output electric wire is connected to the terminal base portion of the electric wire connector.

* * * * *